United States Patent [19]
Christensen, IV et al.

[11] Patent Number: 5,892,098
[45] Date of Patent: Apr. 6, 1999

[54] 3,3-(DISUBSTITUTED)CYCLOHEXAN-1-ONE MONOMERS AND RELATED COMPOUNDS

[75] Inventors: Siegfried B. Christensen, IV, Philadelphia; Joseph M. Karpinski; M. Dominic Ryan, both of Pottstown, all of Pa.; Paul E. Bender, Cherry Hill, N.J.

[73] Assignee: SmithKline Beecham Corporation, Philadelphia, Pa.

[21] Appl. No.: 624,546

[22] PCT Filed: Dec. 21, 1995

[86] PCT No.: PCT/US95/16710

§ 371 Date: Apr. 15, 1997

§ 102(e) Date: Apr. 15, 1997

[87] PCT Pub. No.: WO96/20158

PCT Pub. Date: Jul. 4, 1996

[51] Int. Cl.⁶ .................................................. C07C 69/76

[52] U.S. Cl. .................................. 560/59; 560/43; 564/84; 564/161; 564/162; 564/163; 568/308; 568/329; 514/534; 514/545; 514/617; 514/618

[58] Field of Search .......................... 560/59, 43; 564/84, 564/161, 162, 163; 568/308, 329; 514/534, 545, 617, 618

[56] References Cited

FOREIGN PATENT DOCUMENTS

A 27 48 466  3/1978  Germany .

*Primary Examiner*—Paul J. Killos
*Attorney, Agent, or Firm*—James M. Kanagy; Stephen Venetianer

[57] ABSTRACT

This invention relates to derivatives of 3,3-(disubstituted) cyclohexan-1-one monomers and related compounds which are useful for treating allergic and inflammatory diseases.

9 Claims, No Drawings

3,3-(DISUBSTITUTED)CYCLOHEXAN-1-ONE MONOMERS AND RELATED COMPOUNDS

FIELD OF INVENTION

The present invention relates to novel 3,3-(disubstituted) cyclohexan-1-one monomers and related compounds, pharmaceutical compositions containing these compounds, and their use in treating allergic and inflammatory diseases and for inhibiting the production of Tumor Necrosis Factor (TNF).

BACKGROUND OF THE INVENTION

Bronchial asthma is a complex, multifactorial disease charactized by reversible narrowing of the airway and hyperreactivity of the respiratory tract to external stimuli.

Identification of novel therapeutic agents for asthma is made difficult by the fact that multiple mediators are responsible for the development of the disease. Thus, it seems unlikely that eliminating the effects of a single mediator will have a substantial effect on all three components of chronic asthma. An alternative to the "mediator approach" is to regulate the activity of the cells responsible for the pathophysiology of the disease.

One such way is by elevating levels of cAMP (adenosine cyclic 3',5'-monophosphate). Cyclic AMP has been shown to be a second messenger mediating the biologic responses to a wide range of hormones, neurotransmitters and drugs; [Krebs Endocrinology Proceedings of the 4th International Congress Excerpta Medica, 17–29, 1973]. When the appropriate agonist binds to specific cell surface receptors, adenylate cyclase is activated, which converts $Mg^{+2}$-ATP to cAMP at an accelerated rate.

Cyclic AMP modulates the activity of most, if not all, of the cells that contribute to the pathophysiology of extrinsic (allergic) asthma As such, an elevation of cAMP would produce beneficial effects including: 1) airway smooth muscle relaxation, 2) inhibition of mast cell mediator release, 3) suppression of neutrophil degranulation, 4) inhibition of basophil degranulation, and 5) inhibition of monocyte and macrophage activation. Hence, compounds that activate adenylate cyclase or inhibit phosphodiesterase should be effective in suppressing the inappropriate activation of airway smooth muscle and a wide variety of inflammatory cells. The principal cellular mechanism for the inactivation of cAMP is hydrolysis of the 3'-phosphodiester bond by one or more of a family of isozymes referred to as cyclic nucleotide phosphodiesterases (PDEs).

It has now been shown that a distinct cyclic nucleotide phosphodiesterase (PDE) isozyme, PDE IV, is responsible for cAMP breakdown in airway smooth muscle and inflammatory cells. [Torphy, "Phosphodiesterase Isozymes: Potential Targets for Novel Anti-asthmatic Agents" in New Drugs for Asthma, Barnes, ed. IBC Technical Services Ltd., 1989]. Research indicates that inhibition of this enzyme not only produces airway smooth muscle relaxation, but also suppresses degranulation of mast cells, basophils and neutrophils along with inhibiting the activation of monocytes and neutrophils. Moreover, the beneficial effects of PDE IV inhibitors are markedly potentiated when adenylate cyclase activity of target cells is elevated by appropriate hormones or autocoids, as would be the case in vivo. Thus PDE IV inhibitors would be effective in the asthmatic lung, where levels of prostaglandin $E_2$ and prostacyclin (activators of adenylate cyclase) are elevated. Such compounds would offer a unique approach toward the pharmacotherapy of bronchial asthma and possess significant therapeutic advantages over agents currently on the market.

The compounds of this invention also inhibit the production of Tumor Necrosis Factor (INF), a serum glycoprotein. Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, cachexia secondary to human acquired immune deficiency syndrome (AIDS), AIDS, ARC (AIDS related complex), keloid formation, scar tissue formation, Crohn's disease, ulcerative colitis, or pyresis, in addition to a number of autoimmune diseases, such as multiple sclerosis, autoimmune diabetes and systemic lupus erythematosis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell-mediated immunity is impaired and infected individuals manifest severe opportunistic infections and/or unusual neoplasms. HIV entry into the T lymphocyte requires T lymphocyte activation. Viruses such as HIV-1 or HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication.

Cytokines, specifically TNF, are implicated in activated T-cell-mediated HIV protein expression and/or virus replication by playing a role in maintaining T lymphocyte activation. Therefore, interference with cytokine activity such as by inhibition of cytokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T cells, are targets for viral replication and the level of viral replication is dependent upon the activation state of the cells. [See Rosenberg et al., The Immunopathogenesis of HIV Infection, Advances in Immunology, Vol. 57, 1989]. Monokines, such as TNF, have been shown to activate HIV replication in monocytes and/or macrophages [See Poli et al., Proc. Natl Acad. Sci., 87:782–784, 1990], therefore, inhibition of monoline production or activity aids in limiting HIV progression as stated above for T cells.

TNF has also been implicated in various roles with other viral infections, such as the cytomegalovirus (CMV), influenza virus, adenovirus, and the herpes virus for similar reasons as those noted.

TNF is also associated with yeast and fungal infections. Specifically *Candida albicans* has been shown to induce TNF production in vitro in human monocytes and natural killer cells. [See Riipi et al., Infection and Immunity, 58(9):2750–54, 1990; and Jafari et al., Journal of Infectious Diseases, 164:389–95, 1991. See also Wasan et al., Antimicrobial Agents and Chemotherapy, 35,(10):2046–48, 1991; and Luke et al., Journal of Infectious Diseases, 162:211–214,1990].

The ability to control the adverse effects of TNF is furthered by the use of the compounds which inhibit TNF in mammals who are in need of such use. There remains a need for compounds which are useful in treating TNF-mediated disease states which are exacerbated or caused by the excessive and/or unregulated production of TNF.

SUMMARY OF THE INVENTION

In a first aspect, this invention relates to compounds of Formula (1):

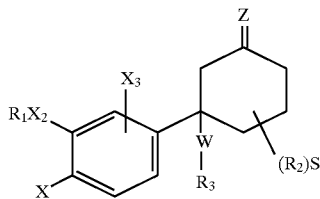

wherein:

$R_1$ is $-(CR_4R_5)_nC(O)O(CR_4R_5)_mR_6$, $-(CR_4R_5)_nC(O)NR_4(CR_4R_5)_mR_6$, $-(CR_4R_5)_nO(CR_4R_5)_mR_6$, or $-(CR_4R_5)_rR_6$ wherein the alkyl moieties may be unsubstituted or substituted with one or more fluorines;

m is 0 to 2;

n is 0 to 4;

r is 0 to 6;

$R_4$ and $R_5$ are independently hydrogen or $C_{1-2}$ alkyl $R_6$ is hydrogen, methyl, hydroxyl aryl, halo substituted aryl, aryloxy $C_{1-3}$ alkyl, halo substituted aryloxy $C_{1-3}$ alkyl, indanyl indenyl $C_{7-11}$ polyeycloalkyl tetrahydrofuranyl, furanyl, tetrahydropyranyl pyranyl, tetrahydrothienyl, thienyl tetrahydrothiopyranyl, thiopyranyl, $C_{3-6}$ cycloalkyl, or a $C_{4-6}$ cycloalkyl containing one or two unsaturated bonds, wherein the cycloalkyl or heterocyclic moiety may be unsubstituted or substituted by 1 to 3 methyl groups, one ethyl group, or an hydroxyl group;

provided that:

a) when $R_6$ is hydroxyl, then m is 2; or b) when $R_6$ is hydroxyl then r is 2 to 6; or c) when $R_6$ is 2-tetrahydropyranyl, 2-tetrahydrothiopyranyl, 2-tetrahydrofuranyl, or 2-tetrahydrothienyl, then m is 1 or 2; or d) when $R_6$ is 2-tetrahydropyranyl, 2-tetrahydrothiopyranyl, 2-tetrahydrofuranyl, or 2-etrahydrothienyl, then r is 1 to 6;

e) when n is 1 and m is 0, then $R_6$ is other than H in $-(CR_4R_5)_nO(CR_4R_5)_mR_6$;

X is $YR_2$, fluorine, $NR_4R_5$, or formyl amine;

Y is O or $S(O)_{m'}$;

m' is 0, 1, or 2;

$X_2$ is O or $NR_8$;

$X_3$ is hydrogen or X;

$R_2$ is independently selected from $-CH_3$ or $-CH_2CH_3$ unsubstituted or substituted by 1 or more fluorines;

s is 0 to 4;

$R_3$ is $COOR_{14}$, $C(O)NR_4R_{14}$ or $R_7$;

W is alkyl of 2 to 6 carbons, alkenyl of 2 to 6 carbon atoms or alkynyl of 2 to 6 carbon atoms;

Z is O, $NR_7$, $NCR_4R_5C_{2-6}$ alkenyl, $NOR_{14}$, $NOR_{15}$, $NOCR_4R_5C_{2-6}$ alkenyl, $NNR_4R_{14}$, $NNR_4R_{15}$, NCN, $NNR_8C(O)NR_8R_{14}$, $NNR_8C(S)NR_8R_{14}$, or =Z is 2-(1,3-dithiane), 2-(1,3-dithiolane), dimethylthio ketal, diethylthio ketal, 2-(1,3-dioxolane), 2(1,3-dioxane), 2-(1,3-oxathiolane), dimethyl ketal or diethyl ketal;

$R_7$ is $-(CR_4R_5)_qR_{12}$ or $C_{1-6}$ alkyl wherein the $R_{12}$ or $C_{1-6}$ alkyl group is unsubstituted or substituted one or more times by methyl or ethyl unsubstituted or substituted by 1–3 fluorines, $-F$, $-Br$, $-Cl$, $-NO_2$, $-NR_{10}R_{11}$, $-C(O)R_8$, $-CO_2R_8$, $-O(CH_2)_{2-4}OR_8$, $-(CH_2)_qR_8$, $-CN$, $-C(O)NR_{10}R_{11}$, $-O(CH_2)_qC(O)NR_{10}R_{11}$, $-O(CH_2)_qC(O)R_9$, $-NR_{10}C(O)NR_{10}R_{11}$, $-NR_{10}C(O)R_{11}$, $-NR_{10}C(O)OR_9$, $-NR_{10}C(O)R_{13}$, $-C(NR_{10})NR_{10}R_{11}$, $-C(NCN)NR_{10}R_{11}$, $-C(NCN)SR_9$, $-NR_{10}C(NCN)SR_9$, $-NR_{10}C(NCN)NR_{10}R_{11}$, $-NR_{10}S(O)_2R_9$, $-S(O)_{m'}R_9$, $-NR_{10}C(O)C(O)NR_{10}R_{11}$, $-NR_{10}C(O)C(O)R_{10}$, or $R_{13}$;

q is 0, 1, or 2;

$R_{12}$ is $R_{13}$, $C_3-C_7$ cycloalkyl, (2-, 3- or 4-pyridyl), pyrimidyl, pyrazolyl, (1- or 2-imidazolyl), pyrrolyl, piperazinyl, piperidinyl, morpholinyl, furanyl, (2- or 3-thienyl), quinolinyl, naphthyl, or phenyl;

$R_8$ is hydrogen or $R_9$;

$R_9$ is $C_{1-4}$ alkyl unsubstituted or substituted by one to three fluorines;

$R_{10}$ is $OR_8$ or $R_{11}$;

$R_{11}$ is hydrogen, or $C_{1-4}$ alkyl unsubstituted or substituted by one to three fluorines; or when $R_{10}$ and $R_{11}$ are as $NR_{10}R_{11}$ they may together with the nitrogen form a 5 to 7 membered ring optionally containing at least one additional heteroatom selected from O, N, or S;

$R_{13}$ is a substituted or unsubstituted heteroaryl group selected from the group consisting of oxazolidinyl, oxazolyl, thiazolyl, pyrazolyl, triazolyl, tetrazolyl, imidazolyl, imidazolidinyl, thiazolidinyl, isoxazolyl, oxadiazolyl, and thiadiazolyl, and where $R_{13}$ is substituted on $R_{12}$ or $R_{13}$ the rings are connected through a carbon atom and each second $R_{13}$ ring may be unsubstituted or substituted by one or two $C_{1-2}$ alkyl groups unsubstituted or substituted on the methyl with 1 to 3 fluoro atoms;

$R_{14}$ is hydrogen or $R_7$; or when $R_8$ and $R_{14}$ are as $NR_8R_{14}$ they may together with the nitrogen form a 5 to 7 membered ring optionally containing one or more additional heteroatoms selected from O, N, or S;

$R_{15}$ is $C(O)R_{14}$, $C(O)NR_4R_{14}$, $S(O)_2R_7$, or $S(O)_2NR_4R_{14}$;

provided that:

(f) $R_7$ is not $C_{1-4}$ alkyl unsubstituted or substituted by one to three fluorines;

or the pharmaceutically acceptable salts thereof.

Another set of compounds of this invention are represented by Formula (II):

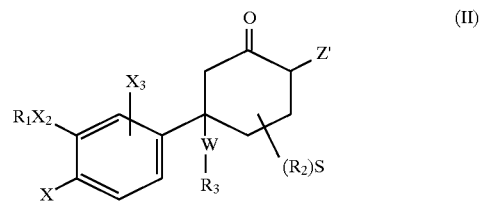

wherein:

$R_1$ is $-(CR_4R_5)_nC(O)O(CR_4R_5)_mR_6$, $-(CR_4R_5)_nC(O)NR_4(CR_4R_5)_mR_6$, $-(CR_4R_5)_nO(CR_4R_5)_mR_6$, or $-(CR_4R_5)_rR_6$ wherein the alkyl moieties may be unsubstituted or substituted with one or more fluorines;

m is 0 to 2;

n is 0 to 4;

r is 0 to 6;

$R_4$ and $R_5$ are independently hydrogen or $C_{1-2}$ alkyl;

$R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl or heterocyclic moiety is unsubstituted or substituted by 1 to 3 methyl groups, an ethyl group, or an hydroxyl group;

provided that:

a) when $R_6$ is hydroxyl, then m is 2; or b) when $R_6$ is hydroxyl, then r is 2 to 6; or c) when $R_6$ is 2-tetrahydropyranyl, 2-tetrahydrothiopyranyl, 2-tetrahydrofuranyl, or 2-tetrahydrothienyl, then m is 1 or 2; or d) when $R_6$ is 2-tetrahydropyranyl, 2-tetrahydrothiopyranyl, 2-tetrahydrofuranyl, or 2-tetrahydrothienyl, then r is 1 to 6;

e) when n is 1 and m is 0, then $R_6$ is other than H in —$(CR_4R_5)_nO(CR_4R_5)_mR_6$;

X is $YR_2$, fluorine, $NR_4R_5$, or formyl amine;

Y is O or $S(O)_{m'}$;

m' is 0, 1, or 2;

$X_2$ is O or $NR_8$;

$X_3$ is hydrogen or X;

$R_2$ is independently selected from —$CH_3$ or —$CH_2CH_3$ unsubstituted or substituted by 1 or more fluorines;

s is 0 to 4;

$R_3$ is $COOR_{14}$, $C(O)NR_4R_{14}$ or $R_7$;

W is alkyl of 2 to 6 carbons, alkenyl of 2 to 6 carbon atoms or alkynyl of 2 to 6 carbon atoms;

Z' is $C(Y')R_{14}$, $C(O)OR_{14}$, $C(Y')NR_{10}R_{14}$, $C(NR_{10})NR_{10}R_{14}$, CN, $C(NOR_8)R_{14}$, $C(O)NR_8NR_8C(O)R_8$, $C(O)NR_8NR_{10}R_{14}$, $C(NOR_{14})R_8$, $C(NR_8)NR_{10}R_{14}$, $C(NR_{14})NR_8R_8$ $C(NCN)NR_{10}R_{14}$, $C(NCN)SR_9$, (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, or 5-oxazolidinyl), (2-, 4-, or 5-thiazolidinyl), or (2-, 4-, or 5-imidazolidinyl); wherein all of the heterocylic ring systems may be optionally substituted one or more times by $R_{14}$;

Y' is O or S;

$R_7$ is —$(CR_4R_5)_qR_{12}$ or $C_{1-6}$ alkyl wherein the $R_{12}$ is phenyl or $C_{1-6}$ alkyl group is unsubstituted or substituted one or more times by $C_{1-2}$ alkyl unsubstituted or substituted by one to three fluorines, —F, —Br, —Cl, —$NO_2$, —$Si(R_4)_3$, —$NR_{10}R_{11}$, —$C(O)R_8$, —$O(CH_2)_{2-4}OR_8$, —$CO_2R_8$, —$OR_8$, —CN, —$C(O)NR_{10}R_{11}$, —$OC(O)NR_{10}R_{11}$, —$OC(O)R_8$, —$NR_{10}C(O)NR_{10}R_{11}$, —$NR_{10}C(O)R_{11}$, —$NR_{10}C(O)OR_9$, —$NR_{10}C(O)R_{13}$, —$C(NR_{10})NR_{10}R_{11}$, —C(NCN)$NR_{10}R_{11}$, —$C(NCN)SR_9$, —$NR_{10}C(NCN)SR_9$, —$NR_{10}C(NCN)NR_{10}R_{11}$, —$NR_{10}S(O)_2R_9$, —$S(O)_{m'}R_9$, —$NR_{10}C(O)C(O)NR_{10}R_{11}$, —$NR_{10}C(O)C(O)R_{10}$, thiazolyl, imidazolyl, oxazolyl, pyrazolyl, triazolyL or tetrazolyl;

q is 0, 1, or 2;

$R_{12}$ is $R_{13}$, $C_{3-7}$ cycloalkyl, (2-, 3- or 4-pyridyl), pyrimidyl, pyrazolyl, (1- or 2-imidazolyl), thiazolyl, triazolyl, pyrrolyl, piperazinyl, piperidinyl, morpholinyl, furanyl, (2- or 3-thienyl), (4 or 5-thiazolyl), quinolinyl, naphthyl, or phenyl;

$R_8$ is independently selected from hydrogen or $R_9$;

$R_9$ is $C_{1-4}$ alkyl unsubstituted or substituted by one to three fluorines;

$R_{10}$ is $OR_8$ or $R_{11}$;

$R_{11}$ is hydrogen, or $C_{1-4}$ alkyl unsubstituted or substituted by one to three fluorines; or when $R_{10}$ and $R_{11}$ are as $NR_{10}R_{11}$ they may together with the nitrogen form a 5 to 7 membered ring optionally containing at least one additional heteroatom selected from O, N, or S;

$R_{13}$ is a substituted or unsubstituted heteroaryl group selected from the group consisting of oxazolidinyl, oxazolyl, thiazolyl, pyrazolyl, triazolyl, tetrazolyl, imidazolyl, imidazolidinyl, thiazolidinyl, isoxazolyl, oxadiazolyl, and thiadiazolyl, and where $R_{13}$ is substituted on $R_{12}$ or $R_{13}$ the rings are connected through a carbon atom and each second $R_{13}$ ring may be unsubstituted or substituted by one or two $C_{1-2}$ alkyl groups unsubstituted or substituted on the methyl with 1 to 3 fluoro atoms;

$R_{14}$ is hydrogen or $R_7$; or when $R_8$ and $R_{14}$ are as $NR_8R_{14}$ they may together with the nitrogen form a 5 to 7 membered ring optionally containing one or more additional heteroatoms selected from O, N, or S;

provided that:

(f) $R_7$ is not $C_{1-4}$ alkyl unsubstituted or substituted by one to three fluorines;

or the pharmaceutically acceptable salts thereof.

This invention also relates to the pharmaceutical compositions comprising a compound of Formula (I) and (II) and a pharmaceutically acceptable carrier or diluent.

The invention also relates to a method of mediation or inhibition of the enzymatic activity (or catalytic activity) of PDE IV in manunals, including humans, which comprises administering to a mammal in need thereof an effective amount of a compound of Formula (I) and (II) as shown above.

The invention further provides a method for the treatment of allergic and inflammatory disease which comprises administering to a mammal, including humans, in need thereof, an effective amount of a compound of Formula (I) and (II).

The invention also provides a method for the treatment of asthma which comprises administering to a mammal, including humans, in need thereof, an effective amount of a compound of Formula (I) and (II).

This invention also relates to a method of inhibiting TNF production in a mammal, including humans, which method comprises administering to a mammal in need of such treatment, an effective TNF inhibiting amount of a compound of Formula (I) and (II). This method may be used for the prophylactic treatment or prevention of certain TNF mediated disease states amenable thereto.

This invention also relates to a method of treating a human afflicted with a human immunodeficiency virus (HIV), which comprises administering to such human an effective TNF inhibiting amount of a compound of Formula (I) and (II).

Compounds of Formula (I) and (II) are also useful in the treatment of additional viral infections, where such viruses are sensitive to upregulation by TNF or will elicit TNF production in vivo.

In addition, compounds of Formula (I) and (II) are also useful in treating yeast and fungal infections, where such yeast and fungi are sensitive to upregulation by TNF or will elicit TNF production in vivo.

DETAILED DESCRIPTION OF THE INVENTION

This invention also relates to a method of mediating or inhibiting the enzymatic activity (or catalytic activity) of PDE IV in a mammal in need thereof and to inhibiting the production of TNF in a mammal in need thereof, which comprises administering to said mammal an effective amount of a compound of Formula (I) and (II).

Phosphodiesterase IV inhibitors are useful in the treatment of a variety of allergic and inflammatory diseases including: asthma, chronic bronchitis, atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and central nervous system disorders such as depression and multi-infarct dementia.

The viruses contemplated for treatment herein are those that produce TNF as a result of infection, or those which are sensitive to inhibition, such as by decreased replication, directly or indirectly, by the TNF inhibitors of Formula (I) and (II). Such viruses include, but are not limited to HIV-1, HIV-2 and HIV-3, cytomegalovirus (CMV), influenza, adenovirus and the Herpes group of viruses, such as, but not limited to, *Herpes zoster* and *Herpes sinplex*.

This invention more specifically relates to a method of treating a mammal, afflicted with a human immunodeficiency virus (HIV), which comprises administering to such mammal an effective TNF inhibiting amount of a compound of Formula (I) and (II).

The compounds of this invention may also be used in association with the veterinary treatment of animals, other than in humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anemia virus, caprine arthritis virus, visna virus, maedi virus and other lentiviruses.

The compounds of this invention are also useful in treating yeast and fungal infections, where such yeast and fungi are sensitive to upregulation by TNF or will elicit TNF production in vivo. A preferred disease state for treatment is fungal meningitis. Additionally, the compounds of Formula (I ) and (II) may be administered in conjunction with other drugs of choice for systemic yeast and fungal infections. Drugs of choice for fungal infections, include but are not limited to the class of compounds called the polymixins, such as Polymycin B, the class of compounds called the imidazoles, such as clotrimazole, econazole, miconazole, and ketoconazole; the class of compounds called the triazoles, such as fluconazole, and itranazole, and the class of compound called the Amphotericins, in particular Amphotericin B and liposomal Amphotericin B.

The compounds of Formula (I) and (II) may also be used for inhibiting and/or reducing the toxicity of an anti-fungal, anti-bacterial or anti-viral agent by administering an effective amount of a compound of Formula (I) and (II) to a mammal in need of such treatment Preferably, a compound of Formula (I) and (II) is administered for inhibiting or reducing the toxicity of the Amphotericin class of compounds, in particular Amphotericin B.

The term "$C_{1-3}$ alkyl", "$_{1-4}$ alkyl", "$C_{1-6}$ alkyl" or "alkyl" groups as used herein is meant to include both straight or branched chain radicals of 1 to 10, unless the chain length is limited thereto, including, but not limited to methyl, ethyl, n-propyl, isopropyl, n-butyl, sec-butyl, isobutyl, tert-butyl, and the like.

"Alkenyl" means both straight or branched chain radicals of 1 to 6 carbon lengths, unless the chain length is limited thereto, including but not limited to vinyl, 1-propenyl, 2-propenyl, or 3-methyl-2-propenyl.

The term "cycloalkyl" or "cycloalkyl alkyl" means groups of 3–7 carbon atoms, such as cyclopropyl, cyclopropylmethyl, cyclopentyl, or cyclohexyl.

"Aryl" or "aralkyl", unless specified otherwise, means an aromatic ring or ring system of 6–10 carbon atoms, such as phenyl, benzyl, phenethyl or naphthyl. Preferably the aryl is monocyclic, i.e, phenyl. The alkyl chain is meant to include both straight or branched chain radicals of 1 to 4 carbon atoms. "Heteroaryl" means an aromatic ring system containing one or more heteroatoms.

"Halo" means all halogens, i.e., chloro, fluoro, bromo, or iodo.

"Inhibiting the production of IL-1" or "inhibiting the production of TNF" means:

a) a decrease of excessive in vivo IL-1 or TNF levels, respectively, in a human to normal levels or below normal levels by inhibition of the in vivo release of IL-1 by all cells, including but not limited to monocytes or macrophages;

b) a down regulation, at the translational or transcriptional level, of excessive in vivo IL-1 or TNF levels, respectively, in a human to normal levels or below normal levels; or c) a down regulation, by inhibition of the direct synthesis of IL-1 or TNF levels as a postranslational event.

The phrase "TNF mediated disease or disease states" means any and all disease states in which TNF plays a role, either by production of TNF itself, or by TNF causing another cytokine to be released, such as but not limited to IL-1 or IL-6. A disease state in which IL-1, for instance is a major component, and whose production or action, is exacerbated or secreted in response to TNF, would therefore be considered a disease state mediated by TNF. As TNF-β (also known as lymphotoxin) has close structural homology with TNF-α (also known as cachectin), and since each induces similar biologic responses and binds to the same cellular receptor, both TNF-α and TNF-β are inhibited by the compounds of the present invention and thus are herein referred to collectively as "TNF" unless specifically delineated otherwise. Preferably TNF-α is inhibited. "Cytokine" means any secreted polypeptide that affects the functions of cells, and is a molecule which modulates interactions between cells in immune, inflammatory, or hematopoietic responses. A cytokine includes, but is not limited to, monokines and lymphokines regardless of which cells produce them. The cytokine inhibited by the present invention for use in the treatment of a HIV-infected human must be a cytokine which is implicated in (a) the initiation and/or maintenance of T cell activation and/or activated T cell-mediated HIV gene expression and/or replication, and/or (b) any cytokine-mediated disease associated problem such as cachexia or muscle degeneration. Preferably, his cytokine is TNF-α.

All of the compounds of Formula (I) and (II) are useful in the method of inhibiting the production of TNF, preferably by macrophages, monocytes or macrophages and monocytes, in a mammal, including humans, in need thereof. All of the compounds of Formula (I) and (II) are useful in the method of inhibiting or mediating the enzymatic or catalytic activity of PDE IV and in treatment of disease states mediated thereby.

Preferred compounds are as follows:

When $R_1$ for the compounds of Formula (I) and (II) is an alkyl substituted by 1 or more halogens, the halogens are preferably fluorine and chlorine, more preferably a $C_{1-4}$ alkyl substituted by 1 or more fluorines. The preferred halo-substituted alkyl chain length is one or two carbons, and most preferred are the moieties —$CF_3$, —$CH_2F$, —$CHF_2$, —$CF_2CHF_2$, —$CH_2CF_3$, and —$CH_2CHF_2$. Preferred $R_1$ substitutents for the compounds of Formula (I) and (II) are $CH_2$-cyclopropyl, $CH_2$-$C_{5-6}$ cycloalkyl, $C_{4-6}$ cycloalkyl unsubstituted or substituted with OH, $C_{7-11}$ polycycloalkyl, (3- or 4-cyclopentenyl), phenyl, tetrahydrofuran-3-yl, benzyl or $C_{1-2}$ alkyl unsubstituted or substituted by 1 or more fluorines, —$(CH_2)_{1-3}C(O)O(CH_2)_{0-2}CH_3$, —$(CH_2)_{1-3}O(CH_2)_{0-2}CH_3$, and —$(CH_2)_{2-4}OH$.

When the $R_1$ term is $(CR_4R_5)$, the $R_4$ and $R_5$ terms are independently hydrogen or alkyl. This allows for branching of the individual methylene units as $(CR_4R_5)_n$ or $(CR_4R_5)_m$; each repeating methylene unit is independent of the other, e.g., $(CR_4R_5)_n$ wherein n is 2 can be —$CH_2CH(—CH_3)$—, for instance. The individual hydrogen atoms of the repeating methylene unit or the branching hydrocarbon can unsubstituted or be substituted by fluorine independent of each other to yield, for instance, the preferred $R_1$ substitutions, as noted above.

When $R_1$ is a $C_{7-11}$ polycycloalkyl, examples are bicyclo[2.2.1]-heptyl, bicyclo[2.2.2]octyl, bicyclo[3.2.1 ]octyl, tricyclo[5.2.1.0$^{2,6}$]decyl, etc. additional examples of which are described in Saccamano et al., WO 87/06576, published Nov. 5, 1987, whose disclosure is incorporated herein by reference in its entirety.

Preferred Z terms are O, NCN, $NR_7$, $NOR_{14}$, $NOR_{15}$, $NNR_4R_{14}$, $NNR_4R_{15}$, $C(CN)_2$, $C(—CN)OC(O)R_9$, $C(—CN)OR_9$, $CR_{14}C(O)OR_8$, $CR_9C(O)NR_{13}R_{14}$, 2-(1,3-dithiane), dimethylthio ketal, 2-(1,3-dioxolane), or dimethyl ketal. More preferred are O, $NR_7$, $NOR_{14}$, $NOR_{15}$, and 2-(1,3-dioxolane).

Preferred X groups for Formula (I) and (II) are those wherein X is $YR_2$ and Y is oxygen. The preferred $X_2$ group for Formula (I) and (II) is that wherein $X_2$ is oxygen. The preferred $X_3$ group for Formula (I) and (II) is that wherein $X_3$ is hydrogen. Preferred $R_2$ groups, where applicable, is a $C_{1-2}$ alkyl unsubstituted or substituted by 1 or more halogens. The halogen atoms are preferably fluorine and chlorine, more preferably fluorine. More preferred $R_2$ groups are those wherein $R_2$ is methyl, or the fluoro-substituted alkyls, specifically a $C_{1-2}$ alkyl, such as a —$CF_3$, —$CHF_2$, or —$CH_2CHF_2$ moiety. Most preferred are the —$CHF_2$ and —$CH_3$ moieties.

W is preferably alkyl, alkenyl or alkynyl of 3 to 5 carbon atoms, and where it is alkenyl or alkynyl, that one or two double or triple bonds be present.

Z' is preferably $COOR_{14}$.

Preferred $R_7$ moieties include $R_{13}$, unsubstituted or substituted —$(CH_2)_{0-2}$(2-, 3- or 4-pyridyl), $(CH_2)_{1-2}$(2-imidazolyl), $(CH_2)_2$(4-morpholinyl), $(CH_2)_2$(4-piperazinyl), $(CH_2)_{1-2}$(2-thienyl), $(CH_2)_{1-2}$(4-thiazolyl), unsubstituted or substituted pyrimidinyl, and substituted or unsubstituted $(CH_2)_{0-2}$phenyl.

Preferred rings when $R_{10}$ and $R_{11}$ in the moiety —$NR_{10}R_{11}$ together with the nitrogen to which they are attached form a 5 to 7 membered ring optionally containing at least one additional heteroatom selected from O, N, or S include, but are not limited to 1-imidazolyl, 2-($R_8$)-1-imidazolyl, 1-pyrazolyl, 3-($R_8$)-1-pyrazolyl, 1-triazolyl, 2-triazolyl, 5-($R_8$)-1-triazolyl, 5-($R_8$)-2-triaolyl, 5-($R_8$)-1-tetrazolyl, 5-($R_8$)-2-tetrazolyl, 1-tetrazolyl, 2-tetrazloyl, morpholinyl, piperazinyl, 4($R_8$)-1-piperazinyl or pyrrolyl ring.

Preferred rings when $R_8$ and $R_{14}$ in the moiety —$NR_8R_{14}$ together with the nitrogen to which they are attached may form a 5 to 7 membered ring optionally containing at least one additional heteroatom selected from O, N, or S include, but are not limited to 1-imidazolyl, 1-pyrazolyl, 1-triazolyl, 2-triazolyl, 1-tetrazolyl, 2-tetrazolyl, morpholinyl, piperazinyl, and pyrrolyl. The respective rings may be additionally substituted, where applicable, on an available nitrogen or carbon by the moiety $R_7$ as described herein for Formula (I) and (II). Illustrations of such carbon substitutions includes, but is not limited to, 2-($R_7$)-1-imindazolyl, 4-($R_7$)-1-imidazolyl, 5-($R_7$)-1-imidazolyl, 3-($R_7$)-1-pyrazolyl, 4-($R_7$)-1-pyrazolyl, 5-($R_7$)-1-pyrazolyl, 4-($R_7$)-2-triazolyl, 5-($R_7$)-2-triazolyl, 4-($R_7$)-1-triazolyl, 5-($R_7$)-1-triazolyl, 5-($R_7$)-1-tetrazolyl, and 5-($R_7$)-2-tetrazolyl. Applicable nitrogen substitution by $R_7$ includes, but is not limited to, 1-($R_7$)-2-etrazolyl, 2-($R_7$)-1-tetrazolyl, 4-($R_7$)-1-piperazinyl. Where applicable, the ring may be substituted one or more times by $R_7$.

Preferred groups for $NR_8R_{14}$ which contain a heterocyclic ring are 5-($R_{14}$)-1-tetrazolyl, 2-($R_{14}$)-1-imidazolyl, 5-($R_{14}$)-2-tetrazolyl, 4-($R_{14}$)-1-piperazinyl, or 4-($R_{15}$)-1-piperazinyl.

Preferred rings for $R_{13}$ include (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, 5-oxazolidinyl), (2-, 4-, or 5-thiazolidinyl), or (2-, 4, or 5-imidazolidinyl).

When the $R_7$ group is unsubstituted or substituted by a heterocyclic ring such as imidazolyl, pyrazolyl, triazolyl, tetrazolyl, or thiazolyl, the heterocyclic ring itself may be unsubstituted or substituted by $R_8$ either on an available nitrogen or carbon atom, such as 1-($R_8$)-2-imidazolyl, 1-($R_8$)-4-imidazolyl, 1-($R_8$)-5-imidazolyl, 1-($R_8$)-3-pyrazolyl, 1-($R_8$)-4-pyrazolyl, 1-(R8)-5-pyrazolyl, 1-($R_8$)4-triazolyl, or 1-($R_8$)-5-triazolyl. Where applicable, the ring may be substituted one or more times by $R_8$.

W is preferably alkyl, alkenyl or alkynyl of 3 to 5 carbon atoms, and where it is alkenyl or alkynyl, that one or two double or triple bonds be present It is most preferred that W is ethynyl or 1,3-butadiynyl.

Preferred are those compounds of Formula (I) and (II) wherein $R_1$ is —$CH_2$-cyclopropyl, —$CH_2$—$C_{5-6}$ cycloalkyl unsubstituted or substituted with OH, —$C_{4-6}$ cycloalkyl unsubstituted or substituted with OH, tetrahydrofuran-3-yl, (3- or 4-cyclopentenyl), benzyl or $C_{1-2}$ alkyl unsubstituted or substituted by 1 or more fluorines, and —$(CH_2)_{2-4}$ OH; $R_2$ is methyl or fluor-substituted alkyl, $R_3$ is $R_7$ where $R_7$ is an unsubstituted or substituted aryl or heteroaryl ring, X is $YR_2$, and Z is O, $NR_7$.

Most preferred are those compounds wherein $R_1$ is —$CH_2$-cyclopropyl, -cyclopentyl, -3-hydroxycyclopentyl, methyl or $CF_2H$; X is $YR_2$; Y is oxygen; $X_2$ is oxygen; $X_3$ is hydrogen; $R_2$ is $CF_2H$ or methyl, W is ethynyl or 1,3-butadiynyl, $R_3$ is a substituted or unsubstituted pyrimidinyl ring, and Z is O, $NR_7$.

Pharmaceutically acceptable salts of the instant compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. The parent compound, dissolved in a suitable solvent, is treated with an excess of an organic or inorganic acid, in the case of acid addition salts of a base, or an excess of organic or inorganic base where the molecule contains a COOH for example.

Pharmaceutical compositions of the present invention comprise a pharmaceutical carrier or diluent and some amount of a compound of the Formula (I) and (II). The compound may be present in an amount to effect a physiological response, or it may be present in a lesser amount such that the user will need to take two or more units of the composition to effect the treatment intended. These compositions may be made up as a solid, liquid or in a gaseous form. Or one of these three forms may be transformed to another at the time of being administered such as when a solid is delivered by aerosol means, or when a liquid is delivered as a spray or aerosol.

The nature of the composition and the pharmaceutical carrier or diluent will, of course, depend upon the intended route of administration, for example parenterally, topically, orally or by inhalation.

For topical administration the pharmaceutical composition will be in the form of a cream, ointment, liniment, lotion, pastes, aerosols, and drops suitable for administration to the skin, eye, ear, or nose.

For parenteral admnistration the pharmaceutical composition will be in the form of a sterile injectable liquid such as an ampule or an aqueous or non-aqueous liquid suspension.

For oral administration the pharmaceutical composition will be in the form of a tablet, capsule, powder, pellet, atroche, lozenge, syrup, liquid, or emulsion.

When the pharmaceutical composition is employed in the form of a solution or suspension, examples of appropriate pharmaceutical carriers or diluents include: for aqueous systems, water, for non-aqueous systems, ethanol, glycerin, propylene glycol corn oil, cottonseed oil, peanut oil, sesame oil, liquid parafins and mixtures thereof with water, for solid systems, lactose, kaolin and mannitol; and for aerosol systems, dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions.

The pharmaceutical preparations thus described are made following the conventional techniques of the pharmaceutical chemist as appropriate to the desired end product.

In these compositions, the amount of carrier or diluent will vary but preferably will be the major proportion of a suspension or solution of the active ingredient. When the diluent is a solid it may be present in lesser, equal or greater amounts than the solid active ingredient.

Usually a compound of formula I is administered to a subject in a composition comprising a nontoxic amount sufficient to produce an inhibition of the symptoms of a disease in which leukotrienes are a factor. Topical formulations will contain between about 0.01 to 5.0% by weight of the active ingredient and will be applied as required as a preventative or curative agent to the affected area. When employed as an oral, or other ingested or injected regimen, the dosage of the composition is selected from the range of from 50 mg to 1000 mg of active ingredient for each administration. For convenience, equal doses will be administered 1 to 5 times daily with the daily dosage regimen being selected from about 50 mg to about 5000 mg.

It will be recognized that some of the compounds of Formula (I) and (II) may exist in both racemic and optically active forms; some may also exist in distinct diastereomeric forms possessing distinct physical and biological properties. All of these compounds are considered to be within the scope of the present invention.

Compounds of Formula (I) where Z is O and (II) may exist in a tautomeric form, such as the enol form This may be represented by the =O being exocyclic to the cyclohexane ring or

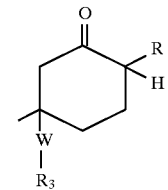

as contrasted to the endocyclic or —C(—OH)=C(—R)— moiety wherein the cyclohexane ring is now unsaturated in the 1–2 position, i.e. cyclohex-1-ene, or

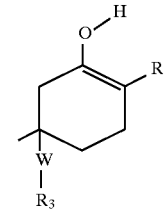

and R is Z in Formula (I). It is also recognized that the 2-position of the ring in the exocyclic form can be substituted (R) such as in the compounds of Formula (I).

The following examples are given to further illustrate the described invention. These examples are intented solely for illustrating the invention and should not be read to limit the invention in any manner. Reference is made to the claims for what is reserved to the inventors hereunder.

No unacceptable toxicological effects are expected when these compounds are administered in accordance with the present invention.

Methods of Preparation Synthetic Scheme(s) With Textual Description

Compounds of Formula (I) may be prepared by the processes disclosed herein which comprise reacting a terminal acetylene as, e.g., compound 1-Scheme 1, with an aryl halide, such as phenyl iodide, in the presence of a suitable catalyst, such as a copper(I) halide and a bivalent or zerovalent palladium compound in the presence of, e.g., triphenylphosphine, in a suitable solvent, such as an amine, as in the procedure of Brandsma et al. (Syn. Comm., 1990, 20, 1889), followed by hydrolysis of the ketal protecting group under standard conditions, provides a compound of the Formula 2-Scheme 1. Compounds of the Formula 1-Scheme 1 may be prepared by procedures analogous to those described in co-pending U.S. patent application Ser. No. 08/130,215 filed Oct. 10, 1993 and its progeny filed as a continuation via the PCT.

Scheme 1

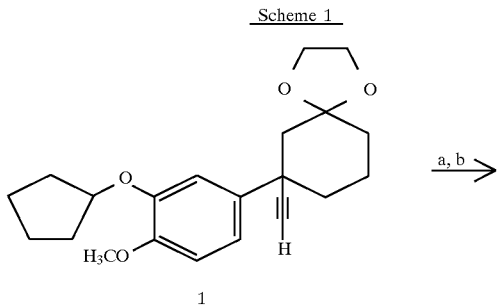

a) Pd(PPh$_3$)$_4$, PPh$_3$, CuI, C$_6$H$_5$I, piperidine;
b) pyridinium p-toluenesulfonate, (H$_3$C)$_2$CO/H$_2$O Alternatively, compounds of Formula (I) may be prepared by reacting a terminal acetylene as, e.g., compound 1-Scheme 2, with an appropriate halide, R$_3$X, wherein R$_3$ represents R$_3$ as defined in relation to Formula (I) or a group convertible to R$_3$, in the presence of a suitable catalyst, such as a copper (I) halide and a bivalent or zerovalent palladium compound in the presence of, e.g., triphenylphosphine, in a suitable solvent, such as an amine, as in the procedure of Brandsma et al. (Syn. Comm., 1990, 20, 1889), to provide a compound of the Formula 2-Scheme 2; such compounds of the Formula (1) may then be converted to other compounds of the Formula (I) by standard manipulation of the functional groups on the R$_3$ moiety. Compounds of the Formula 1-Scheme 2 may be prepared by procedures analogous to those described in co-pending U.S. patent application Ser. No. 08/130,215 filed Oct. 10, 1993 and its progeny filed as a continuation via the PCT.

Scheme 2

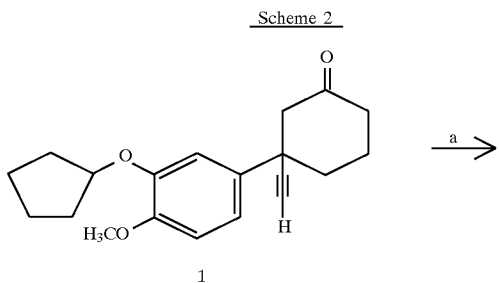

-continued
Scheme 2

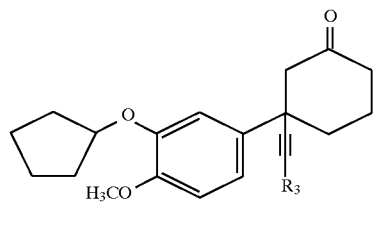

a) Pd(PPh$_3$)$_4$, PPh$_3$, CuI, R$_3$X, piperidine

Alternatively, oxidative carbonylation of a terminal acetylene as, e.g., compound 1-Scheme 3, using an appropriate metal salt, such as a copper salt with a catalytic amount of a palladium salt, in the presence of a suitable base as an acid trap, such as sodium acetate, in a suitable alcohol, such as methanol, as in the method of Tsuji et al. (Tet Lett, 1980, 21, 849), followed by hydrolysis of the methyl ester under standard conditions, then provides the compound of the Formula (I) (2-Scheme 3); such compounds of the Formula (I) may then be converted to other compounds of the Formula (I) by standard manipulation of the carboxylic ester moiety.

Scheme 3

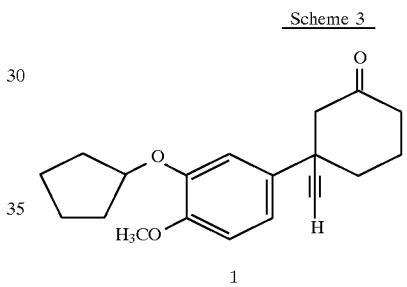

a) PdCl$_2$, CuCl$_2$, NaO$_2$CCH$_3$, CO, CH$_3$OH

Compounds of Formula (II) may be prepared by processes analogous to those in Schemes 1, 2 and 3 above, as illustrated in Scheme 4 wherein. Depending upon the exact nature of the Z' groups of the compounds of ty require protection during the coupling steps described herein as, e.g., a compound of the Formula (II) wherein =O is a dimethyl ketal or 2-(1,3-dioxolane), followed by deprotection and then reaction by the synthetic procedures described in co-pending U.S. patent application Ser. No. 08/130,215 filed Oct. 10, 1993 and its progeny filed as a continuation via the PCT, to provide the Formula (II) compound; likewise, the Z' group may require protection during the coupling steps, followed by deprotection to provide the Formula (II) compound and such protective groups are well known to those skilled in the art. (See: Greene, T. and Wuts, P. G. M., Protecting Groups in Organic Synthesis, 2nd Ed., John Wiley and Sons, New York, 1991.)

Scheme 4

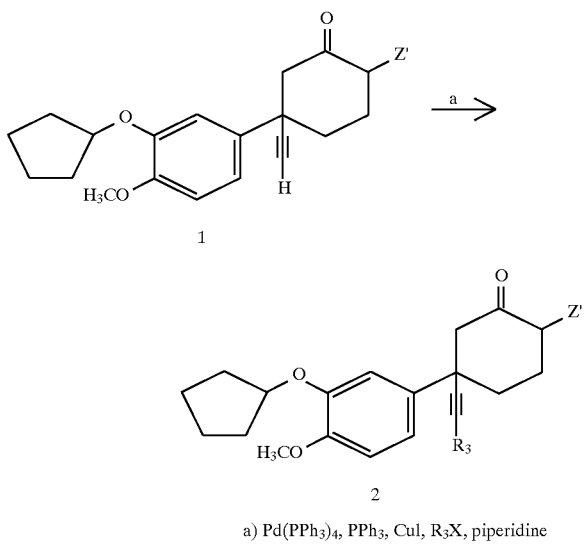

a) Pd(PPh$_3$)$_4$, PPh$_3$, CuI, R$_3$X, piperidine

Preparation of the remaining compounds of the Formulas (I) and (II) may be accomplished by procedures analogous to those described above and in the Examples, infra.

It will be recognized that compounds of the Formulas (I) and (II) may exist in distinct diastereomeric forms possessing distinct physical and biological properties; such isomers may be separated by standard chromatographic methods.

Experimentals

EXAMPLE 1

Preparation of 3-(carbomethoxyethynyl)-3-(3-cyclopentyloxy-4-methoxyphenyl)-cyclohexan-1-one 1a) 3-(3-cyclopentyloxy-4-methoxyphenyl)-3-trimethylsilylethynyl cyclohexan-1-one n-Butyllithium (2.45 M in hexanes, 5.7 mL, 13.96 mmol) was added dropwise over 5 min to a solution of trimethylsilylacetylene ( 1.97 mL, 13.96 mmol) dissolved in dry ether (30 mL) at −45° C. under an argon atmosphere. After 1.5 h, this solution was cannulated into a solution of dimethylaluminum chloride (1.0 M in hexanes, 13.96 mL, 13.96 mmol). After 3.5 h at room temperature, the mixture was filtered through Celite® under an argon atmosphere. In a separate flask, diisobutylaluminum hydride (1.0 M in toluene, 1.4 mL, 1.4 mmol) was added dropwise to a stirred mixture of nickel acetylacetonate (360 mg, 1.4 mmol) in dry ether (25 mL) at 0° C. under an argon atmosphere. After 10 min, the mixture was further cooled to −10° C. and the solution of aluminum acetylide was added via cannulation over 15 min. 3-(3-cyclopentyloxy-4-methoxyphenyl) cyclohex-2-en-1 -one (2.0 g, 6.98 mmol, prepared as described in U.S. Pat. No. 5,362,915) dissolved in dry ether (70 mL) was added dropwise over 20 min. After 18 h at room temperature, the mixture was poured into a 100 mL saturated aqueous solution of potassium phosphate (monobasic) at 0° C., 100 mL of aqueous 3N HCl solution was added and the aqueous layer was extracted twice with ether. The combined extract was washed with brine, was dried (magnesium sulfate) and was evaporated. Purification by flash chromatography, eluting with 2:1 hexanes/ether followed by trituration from ether/hexanes, then firthur purification of the mother liquor by flash chromatography, eluting with 4:1 hexaneslethyl acetate followed by trituration from ether/hexanes, provided a white solid. mp 102–103° C.

1b) 3-(3-cyclopentyloxy-4-methoxyphenyl)-3-ethynylcyclohexan-1-one

A mixture of potassium fluoride (900 mg, 15.6 mmol) and 3-(3-cyclopentyloxy-4-methoxyphenyl)3-trimethylsilylethynyl cyclohexan-1-one (0.3 g, 0.78 mmol) was stirred in dry N,N-dimethylformamide (3 mL) under an argon atmosphere. After 18 h, the solvent was removed in vacuo, the residue was partitioned between water and ethyl acetate, the aqueous layer was extracted twice with ethyl acetate, the combined extract was dried (magnesium sulfate) and was evaporated. Purification by flash chromatography, eluting with 4:1 hexanes/ethyl acetate provided a clear colorless oil . Anal. (C$_{20}$H$_{24}$O$_3$·$^1$/$_{10}$H$_2$O) calcd: C 76.45,H 7.76; found: C 76.32,H 7.60.

1c) 3-(carbomethoxyethynyl)-3-(3-cyclopentyloxy-4-methoxyphenyl)cyclohexan-1-one 3-(3Cyclopentyloxy-4-methoxyphenyl)-3-ethynylcyclohexan-1-one (0.30 g, 0.98 mmol) was dissolved in dry methanol (20 mL) and carbon monoxide was bubbled into the solution for 10 min. A mixture of copper (II) chloride (0.264 g, 1.96 mmol) and sodium acetate trihydrate (0.267 g, 1.96 mmol) was added, then trace palladium (II) chloride was added. After 2.5 h at room temperature, water was added and the methanol was evaporated The aqueous residue was extracted three times with ether, the combined extract was washed with brine, was dried (magnesium sulfate) and was evaporated. Purification by flash chromatography, eluting with 2:1 hexanes/ethyl acetate, provided a pale yellow oil. $^1$H NMR(400 MHz, CDCl$_3$) δ7.0 (d, J=2.3Hz, 1H), 6.95 (dd, J=8.4, 2.3Hz, 1H), 6.84 (d, J=8.4Hz, 1H), 4.78 (m, 1H), 3.84 (s, 3H), 3.76 (s, 3H), 2.82 (d, J=25Hz, 1H), 2.78 (d, J=25Hz, 1H), 2.5–2.1 (m, 5H), 2.0–1.8 (m, 7H), 1.61 (m, 2H).

EXAMPLE 2

Preparation of 3-(carboxyethynyl)-3-(3-cyclopentyloxy-4-methoxyphenyl-4-cyclohexan-1-one 3-(Carbomethoxyethynyl)-3-(3-cyclopentyloxy-4-methoxyphenyl)cyclohexan-1-one (0.14 g, 0.38 mmol) was dissolved in 5:5:2 tetrahydrofuran/methanol/water and treated with powdered sodium hydroxide (0.046 g, 1.114 mmol). After 2 h at room temperature, the mixure was concentrated in vacuo, was diluted with water (5 mL), was acidified with aqueous 3N HCl and was extracted five times with dichloromethane. The combined extract was dried (magnesium sulfate) and was evaporated. Purification by flash chromatography, eluting with 88:10:2 chloroform/methanolacetic acid, provided an oil, which was redissolved and evaporated three times with toluene and two times with chloroform to provide a colorless solid. mp 71–72.5° C.

EXAMPLE 3

Resolution of (+/−)-3-(3-cyclopentyloxy-4-methoxyphenyl-3-ethynyl-cyclohexan-1-one The compound from Example 1b was resolved in the following manner to give enantiomeric oils: HPLC R$_t$=15.5 min (enantiomer 1=E1), 23.2 min (enantiomer 2=E2) (Diacel Chiralpak AS; 21.2×250 mm; hexane:isopropanol, 4:1; 10 mL/min; UV detection at 295 nm).

EXAMPLE 4

Preparation of (+/−) 3-(3-cyclopentyloxy-4-methoxyphenyl)-3-phenylethynyl-cyclohexan-1-one To a solution of the compound of Example 1b (0.125 g, 0.4 mmol) and iodobenzene (0.4 mL, 2.0 mmol) in piperidine (6 mL) under an argon atmosphere was added trace tetrakis(triphenylphosphine)palladium(0), copper(I) iodide and triphenylphosphine. The mixture was refluxed for 5 h, then concentrated in vacuo. The residue was diluted with ethyl acetate (100 mL), was washed with brine, was dried ($M_gSO_4$) and was evaporated. Purification by flash chromatography, eluting with 2:1 hexanes/ethyl acetate, followed by trituration from ether/hexanes, provided the title compound as white solid (0.09 g, 58%), m.p. 90–91° C.

EXAMPLE 5

Preparation of (+/−) 3-(3-cyclopentyloxy-4-methoxyphenyl)-3-(3-carbomethoxyphenyl)ethynylcyclohexan-1-one 5a) methyl 3-iodobenzoate Methyl 3-iodobenzoate was prepared by standard chemistry well known to those versed in the art and is a white solid, m.p. 40–41° C.

5b) (+/−) 3-(3-cyclopentyloxy-4-methoxyphenyl)-3-(3-carbomethoxyphenyl)ethynyl-cyclohexan-1-one To a solution of the compound from Example 1b (0.30 g, 0.96 mmol) and methyl 3-iodobenzoate (0.30 g, 1.15 mmol) in triethylamine (10 mL) under an argon atmosphere was added trace tetrakis(triphenylphosphine)palladium(0), copper(I) iodide and triphenylphosphine. The mixture was refluxed for 0.5 h and was then concentrated in vacua. The residue was partitioned between water and ethyl acetate. The organic phase was dried ($Na_2SO_4$) and was evaporated. Purification by flash chromatography, eluting with 2:1 hexanes/ethyl acetate, provided the title compound as a pale yellow oil (0.35 g, 80%). Anal ($C_{28}H_{30}O_5 \cdot 1.0\ H_2O$) calcd: C, 72.39;H, 6.94; found: C, 72.47; H, 6.80.

EXAMPLE 6

Preparation of (+/−) 3-(3-carboxyphenylethynyl)-3-(3-cyclopentyloxy-4-methoxyphenyl-4-cyclohexan-1-one To a solution of the compound from Example 5(b) in 5:5:2 THF/methanol/water (10 mL) under an argon atmosphere was added sodium hydroxide (0.60 g, 1.5 mmol). The mixture was heated at 60° C. for 2 h and was then concentrated in vacuo. The residue was extracted from 3N HCl with ethyl acetate, was washed with brine, was dried ($MgSO_4$) and was evaporated. Purification by flash chromatography, eluting with 98:2:0.3 chloroform/methanol/acetic acid, provided a white solid, m.p. 71–73° C.

EXAMPLE 7

Preparation of 3-(3-cyclopentyloxy-4-methoxyphenyl)-3[3-(5-methyl-[1,3,4]thiadiazol-2-yl)phenylethynyl]cyclohexan-1-one 7a) 1-iodo-3-(5-methyl-[1,3,4]thiadiazol-2-yl)benzene 1-Iodo-3-(5-methyl-[1,3,4]thiadiazol-2-yl)benzene was prepared by standard chemistry well known to those versed in the art and is white solid, m.p. 86–89° C.

7b) 3-(3-cyclopentyloxy-4-methoxyphenyl)-3-[3-(5-methyl-[1,3,4]thiadiazol-2-yl)phenylethynyl]cyclohexan-1-one To a solution of the compound from Example 3 (E1) (0.10 g, 0.32 mmol) and 1-iodo-3-(5-methyl-[1,3,4]thiadiazol-2-yl)benzene (0.10 g, 0.32 mmol) in triethylamine (5 mL) under an argon atmosphere was added trace tetrakis (triphenylphosphine)palldium(0), copper(I) iodide and triphenylphosphine. The mixture was refluxed for 0.20 h, was cooled to room temperature and was concentrated in vacuo. The residue was partitioned between ethyl acetate and water. The organic phase was washed with brine, was dried ($M_gSO_4$) and was evaporated. Purification by flash chromatography, eluting with 1:1 hexaneslethyl acetate provided the tide compound as a white solid (0.135 g, 87%), m.p. 97–99° C.

The enantiomer was prepared in a similar manner, starting with the compound from Example 3 (E2), as a white solid, m.p. 97–99° C.

EXAMPLE 8

Preparation of 3-(3-cyclopentyloxy-4-methoxyphenyl)-3-[3-(5-methyl-[1,3,4]oxadiazol-2-yl)phenylethynyl]cyclohexan-1-one 8a) 1-iodo-3-(5-methyl-[1,3,4]oxadizol-2-yl)benzene 1-Iodo-3-(5-methyl-[1,3,4]oxadiazol-2-yl)benzene was prepared by standard chemistry well known to those versed in the art and is a white solid, mp. 104–105° C.

8b) 3-(3-cyclopentyloxy4-methoxyphenyl)-3-[3-(5-methyl-[1,3,4]oxadiazol-2-yl)phenylethynyl]cyclohexan-1-one To a solution of the compound from Example 3 (E1) (0.125 g, 0.4 mmol) and 1-iodo-3-(5-methyl-[1,3,4] oxadiazol-2-yl)benzene (0.09 g, 0.32 mmol) in triethylamine (3 mL) under an argon atmosphere was added trace tetrakis (triphenylphosphine)-palladium(0), copper(I) iodide and triphenylphosphine. The mixture was heated at 80° C. for 0.2 h , was cooled to room temperature and was concentrated in vacuo. The residue was partitioned between ethyl acetate and water. The organic phase was washed with brine, was dried ($M_gSO_4$) and was evaporated. Purification by flash chromatography, eluting with 2:1 ethyl acetate/hexanes, followed by recrystallization from ethyl acetate/hexanes, provided the title compound as a white solid (0.11 g, 61%), m.p. 117–119° C.

The enantiomer was prepared in a similar manner, starting with the compound from Example 3 (E2), as a white solid, m.p. 117–119° C.

EXAMPLE 9

Preparation of 3-(3-cyclopentyloxy-4-methoxyphenyl)-3-[3-(3-methyl-[1,2,4]-oxadiazol-5-yl)phenylethynyl]cyclohexan-1-one 9a) 1-iodo-3- (3-methyl-[1,2,4]oxadiazol-5-yl)benzene 1-Iodo-3-(3-methyl-[1,2,4]oxadiazol-5-yl)benzene was prepared by standard chemistry well known to those versed in the art and is a white solid, m.p. 101.5–103° C.

9b) 3-(3-cyclopentyloxy-4-methoxyphenyl)-3-[3-(3-methyl-[1 2,4]oxadiazol-5-yl)phenylethynyl]cyclohexan-1-one To a solution of the compound from Example 3 (E1) (0.125 g, 0.4 mmol) and 1-iodo-3-(3-methyl-[1,2,4] oxadiazol-5-yl)benzene (0.09 g, 0.32 mmol) in triethylamine (3 mL) under an argon atmosphere was added trace tetrakis (triphenylphosphine)-palladium(0), copper(I) iodide and triphenylphosphine. The mixture was heated at 80° C. for 0.2 h, was cooled to room temperature and was concentrated in vacua. The residue was partitioned between ethyl acetate and water. The organic phase was washed with brine, was dried ($M_gSO_4$) and was evaporated. The residue was purified by flash chromatography, eluting with 2:1 hexanes/ethyl acetate, followed by trituration from hexanes/ethyl acetate, to provide the title compound as a white solid, m.p. 122 123° C.

The enantiomer was prepared in a similar manner, starting with the compound from Example 3 (E2), as awhite solid, m.p. 122–123° C.

EXAMPLE 10

Preparation of 3-(3-cyclopentyloxy-4-methoxyphenyl)-3-[3-(5-methyl-[1,2,4]oxadiazol-3-yl)phenylethynyl]cyclohexan-1-one 10a) 1-iodo-3-(5-methyl-[1,2,4]oxadiazol-3-yl)benzene 1-iodo-3-(5-methyl-[1,2,4]oxadiazol-3-yl)benzene was prepared by standard chemistry well known to those versed in the art and is a white solid, m.p. 86–87° C.

10b) 3-(3-cyclopentyloxy-4-methoxyphenyl)-3-[3-(5-methyl-[1,2,4]oxadiazol-3-yl)phenylethynyl]cyclohexan-1-one To a solution of the compound from Example 3 (E1) (0.125 g, 0.4 mmol) and 1-iodo-3-(5-methyl-[1,2,4] oxadiazol-3-yl)benzene (0.09 g, 0.32 mmol) in triethylamine (3 mL) under an argon atmosphere was added trace tetrakis (triphenylphosphine)-palladium(0), copper(I) iodide and triphenylphosphine. The mixture was heated at 80° C. for 0.2 h, was cooled to room temperature and was concentrated in vacuo. The residue was partitioned between ethyl acetate and water. The organic phase was washed with brine, was dried ($M_gSO_4$) and was evaporated. Purification by flash chromatography, eluting with 2:1 hexanes/ethyl acetate, followed by trituration from hexanes/ethyl acetate, provided the title compound as colorless crystals (0.12 g, 67%), m.p. 116–118° C.

The enantiomer was prepared in a similar manner, starting with the compound from Example 3 (E2), as colorless crystals, m.p.116–118° C.

EXAMPLE 11

Preparation of 3-(3-cycopentyloxy-4-methoxyphenyl)-3-(3-cyanophenylethynyl) cyclohexan-1-one To a solution of the compound from Example 3 (E1) (0.125 g, 0.4 mmol) and 3-iodobenzonitrile (Transworld, 0.09 g, 0.4 mmol) in triethylamine (3 mL) under an argon atmosphere was added trace tetrakis(triphenylphosphine) palladium(0), copper(I) iodide and triphenylphosphine. The mixture was heated at 80° C. for 0.2 h, was cooled to room temperature and was concentrated in vacuo. The residue was partitioned between ethyl acetate and water. The organic phase was washed with brine, was dried ($M_gSO_4$) and was evaporated. The residue was purified by flash chromatography, eluting with 2:1 hexanes/ethyl acetate, to provide the title compound as a clear yellow glass (0.12 g, 73%). MS(EI) m/e 414 [M+H]+.

The enantiomer was prepared in similar manner, starting with the compound from Example 3 (E2), as a clear yellow glass.

EXAMPLE 12

Preparation of 3-(3-cyclopentyloxy-4-methoxyphenyl)-3-(3-nitrophenylethynyl) cyclohexan-1-one To a solution of the compound from Example 3 (E1) (0.2 g, 0.64 mmol) and 3-iodonitrobenzene (Aldrich, 0.16 g, 0.64 mmol) in triethylamine (4 mL) under an argon atmosphere was added trace tetrakis(triphenylphosphine)palladium(0), copper(I) iodide and triphenylphosphine. The mixture was heated at 80° C. for 0.2 h, was cooled to room temperature and was concentrated in vacuo. The residue was partitioned between ethyl acetate and water. The organic phase was washed with brine, was dried ($M_gSO_4$) and was evaporated. Purification by flash chromatography, eluting with 3:1 hexanes/ethyl acetate, provided the title compound as yellow solid (0.25 g, 90%), m.p. 46–48° C.

The enantiomer was prepared in a similar manner, starting with the compound from Example 3 (E2), as a yellow solid. m.p. 46–48° C.

EXAMPLE 13

Preparation of 3-(3cyclopentyloxy-4-methoxyphenyl)-3-(2-hydroxvethoxyphenylethynyl) cyclohexan-1-one 13a) 2-hydroxyethoxy-1-iodobenzene 2-hydroxyethoxy-1-iodobenzene was prepared by standard chemistry well known to those versed in the art and is a colorless oil. $^1$H NMR(400 MHz, CDCl$_3$)δ7.77 (dd, J=7.9, 1.3Hz, 1H), 7.3 (t, J=7H, 1H), 6.84 (d, J=7.9Hz, 1H), 6.74 (t, J=7.9 Hz, 1H), 4.13 (t, J=4.3Hz, 2H), 3.99 (t, J=4.3Hz, 2H), 2.2 (br s, 1H).

13b) 3-(3-cyclopentyloxy-4-methoxyphenyl)-3-(2-hydroxyethoxyphenylethynyl)-cyclohexan-1-one To a solution of the compound from Example 3 (E1) (0.25 g, 0.8 mmol) and 2-hydroxyethoxy-1-iodobenzene (0.21 g, 0.8 mmol) in triethylamine (5 mL) under an argon atmosphere was added trace tetrakis(triphenylphosphine) palladium(0), copper(I) iodide and triphenylphosphine. The mixture was heated at 80° C. for 1 h, was cooled to room temperature and was concentrated in vacuo. The residue was partitioned between ethyl acetate and water. The organic phase was washed with brine, was dried ($M_gSO_4$) and was evaporated. Purification by flash chromatography, eluting with 1:1 hexanelethyl acetate, provided the title compound as a white solid (0.05 g, 14%), m.p. 93–94° C.

EXAMPLE 14

Preparation of 3-(3-acetamidophenylethynyl)-3-(3-cyclopentyloxy-4-methoxyphenyl)cyclohexan-1-one 14a) 3-acetamido-1-iodobenzene 3-acetamido-1-iodobenzene was prepared by standard chemistry well known to those versed in the art and is a white solid, m.p. 117–118° C.

14b) 3-(3-acetamidophenylethynyl)-3-(3-cyclopentyloxy-4-methoxyphenyl)cyclohexan-1-one To a solution of the compound from Example 3 (E1) (0.2 g, 0.64 mmol) and 3-acetamido-1-iodobenzene (0.17 g, 0.64 mmol) in triethylamine (5 mL) under an argon atmosphere was added trace tetrakis(triphenylphosphine)palladium(0), copper(I) iodide and triphenylphosphine. The mixture was heated at 80° C. for 0.3 h, was cooled to room temperature and was concentrated in vacuo. The residue was purified by flash chromatography, eluting with 1:1 hexanes/ethyl acetate, to provide the tide compound as tan solid (0.17 g, 60%), m.p. 58–60° C.

EXAMPLE 15

Preparation of 3-(3-cyclopentyloxy-4-methoxyphenyl)-3-(3-methanesulfonamidophenylethynyl)cyclohexan-1-one 15a) 1-iodo-3-methanesulfonamidobenzene 1-iodo-3-methanesulfonamidobenzene was prepared by standard chemistry well known to those versed in the art and is light-pink solid, m.p. 102–103° C.

15b) 3-(3-cyclopentyloxy-4-methoxyphenyl)-3-(3-methanesulfonamidophenylethynyl)cyclohexan-1-one To a solution of the compound from Example 3 (E1) (0.2 g, 0.64 mmol) and 1-iodo-3-methanesulfonamidobenzene (0.19 g, 0.64 mmol) in triethylarine (5 mL) under an argon atmosphere was added trace tetrakis(triphenylphosphine)palladium(0), copper(I) iodide and triphenylphosphine. The mixture was heated at 80° C. for 0.3 h, was cooled to room temperature and was concentrated in vacuo. The residue was purified by flash chromatography, eluting with 1:1 hexanes/ethyl acetate, to provide the title compound as a tan solid (0.18 g, 58%), m.p. 59–62° C.

EXAMPLE 16

Preparation of 3-(3-aminophenylethynyl)-3-(3-cyclopentyloxy-4-methoxyphenyl)cyclohexan-1-one 16a) 1-iodo-3-trifluoroacetamidobenzene 1-iodo-3-trifluoroacetamidobenzene was prepared by standard chemistry well known to those versed in the art and is a white solid, m.p. 120–121° C.

16b) 3-(3-cyclopentyloxy-4- methoxyphenyl)-3-(3-trifluoroacetamidophenylethynyl)-cyclohexan-1-one To a solution of the compound from Example 3 (E1) (0.5 g. 1.6 mmol) and 1-iodo-3-triuoroacetamidobenzene (0.5 g, 1.6 mmol) in triethylamine (10 mL) under an argon atmosphere was added a small amount of tetrakis(triphenylphosphine)palladium(0), copper(I) iodide and triphenylphosphine. The mixture was heated at 80° C. for 0.2 h, was cooled to room temperature and was concentrated in vacuo. The residue was purified by flash chromatography, eluting with 3:1 hexanes/ethyl acetate, to give the title compound as a pale yellow solid (0.62 g, 78%), m.p. 63–65° C.

16c) 3-(3-aminophenylethynyl)-3-(3-cyclopentyloxy-4-methoxyphenyl)cyclohexan-1-one To a solution of 3-(3-cyclopentyloxy4-methoxyphenyl)-3-(3-trifluoroacetamidophenylethynyl)cyclohexan-1-one (0.62 g, 1.24 mmol) in 95:5 methanol/water (10 mL) under an argon atmosphere was added potassium carbonate (0.86 g, 6.2 mmol). The mixture was refluxed for 6 h and was stired for 18 h at room temperature. The solid precipitate was collected and purified by trituration from ethyl acetate/hexanes to provide the title compound as a white solid (0.39 g, 77%), m.p. 100–102° C.

EXAMPLE 17

Using the methods and processes set forth in the foregoing examples, the following compounds can also be made:

3-(3-cyclopentyloxy-4-methoxyphenyl)-3-(2-[3-(5-trifluoromethyl[1,2,4]oxadiazol-3-yl)phenyl]ethynyl)cyclohexan-1-one, 3-(3-cyclopentyloxy-4-methoxyphenyl)-3-(2-[3-(3-trifluoromethyl[1,2,4]oxadiazol-5-yl)phenyl]ethynyl)cyclohexan-1-one, 3-(3-cyclopentyloxy-4-methoxyphenyl)-3-(2-[3-(5-trifluoromethyl[1,3,4]oxadiazol-2-yl)phenyl]ethynyl)cyclohexan-1-one, or 3-(3-cyclopentyloxy-4-methoxyphenyl)-3-(2-[3-(5-trifluoromethyl[1,3,4]thiadiazol-2-yl)phenyl]ethynyl)cyclohexan-1-one.

EXAMPLE 18

Preparation of (+/−)-3-(4-carboxyphenylethynyl)-3-(3-cyclopentyloxy-4-methoxyphenyl)cyclohexan-1-one 18(a) methyl 4-iodobenzoate Methyl 4-iodobenzoate was prepared by standard chemistry well known to those versed in the art and is a cream-colored solid, m.p. 103–105° C.

18(b) (+/−) 3-(4-carbomethoxyphenylethynyl)-3-(3-cyclopentyloxy-4-methoxyphenyl)cyclohexan-1-one To a solution of the compound from Example 1b (0.2 g, 0.64 mmol), methyl 4iodobenzoate (0.17 g, 0.64 mmol) in triethylamine (5 mL) under an argon atmosphere was added trace tetrakis(triphenylphosphine)palladium(0) and copper (I) iodide. The mixture was refluxed for 0.25 h, was cooled to room temperature and was concentrated in vacuo. The residue was purified by flash chromatography, eluting with 3:1 hexanes/ethyl acetate, to provide the title compound as a clear, colorless oil (0.25 g, 87%).

18(c) (+/−) 3-(4-carboxyphenylethynyl)-3-(3-cyclopentyloxy-4-methoxyphenyl)cyclohexan-1-one To a solution of the compound from Example 17b (0.25 g, 0.55 mmol) in 5:5:2 tetrahydrofuran/methanol/water (5 mL) under an argon atmosphere was added sodium hydroxide (1.1 mmol, 0.04 g). The mixture was heated at 60° C. for 2 h, was cooled to room temperature and was acidified with 3N hydrochloric acid. The aqueous phase was extracted three times with chloroform, was dried (magnesium sulfate) and was evaporated. The residue was recrystallized from hexanes/ethyl acetate to provide the title compound as a white solid (0.18 g, 78%), m.p. 102–104° C.

EXAMPLE 19

Preparation of 3-(3-cyclopentyloxy-4-methoxyphenyl)3-[3-(5-trifluoromethyl-[1,2,4]oxadiazol-3-yl)phenylethynyl)cyclohexan-1-one 19(a) 3-(3-iodophenyl)-5-trifluoromethyl-[1,2,4]oxadiazole 3-(3-Iodophenyl)-5-trifluoromethyl-[1,2,4]oxadiazole was prepared by standard chemistry well known to those versed in the art and is a white solid, mp 36–37° C.

19(b) 3-(3-cyclopentyloxy-4-methoxyphenyl)3-[3-(5-trifluoromethyl-[1,2,4]oxadiazol-3-yl)phenylethynyl)cyclohexan-1-one A stirred mixture of the compound from Example 3 (E1, 0.200 g, 0.64 mmol) and 3-(3-iodophenyl)-5-trifluoromethyl-[1,2,4]oxadiazole (0.220 g, 0.64 mmol) in dry triethylamine (5 mL) was treated under an argon atmosphere with trace tetrakis(triphenylphosphine)palladium and copper(I) iodide. The mixture was refluxed for 0.2 h, was cooled to room temperature and was evaporated.The residue was adsorbed onto silica gel and was purified by flash chromatography eluting with 3:1 hexanes/ethyl acetate and recrystallization from cold hexanes provided the title compound as a white solid (0.27 g, 83%), mp 99–100° C. Anal. ($C_{29}H_{27}F_3N_2O_4$) calcd: C 66.40,H 5.19, N 5.304; found: C 66.46,H 5.35, N 5.15.

EXAMPLE 20

Preparation of (+) and (−) 3-(3-cyclopentyloxy-4-methoxyphenyl)-3-phenylethynylcyclohexan-1-one A stirred mixture of the compound from Example 3 (E 1, 0.13 g, 0.40 mmol) and iodobenzene (0.40 g, 2.0 mmol) in dry piperidine (6 mL) was treated under an argon atmosphere with trace tetrakis(triphenylphosphine)palladium(0) and copper(I) iodide. The mixture was refluxed for 5 h, was cooled to room temperature and was evaporated. The residue was dissolved in ethyl acetate (100 mL), was washed twice with brine, was dried (magnesium sulfate) and was evaporated. Purification by flash chromatography eluting with 2:1 hexanes/ether, and trituration from ether/hexanes provided the title compound as a white solid (0.03 g, 19%), m.p. 90–91° C.

The enantiomer was prepared in a similar, starting with the compound from Example 3 (E2), as a white solid (0.09 g, 58%), m.p. 90–91° C.

EXAMPLE 21

Preparation of 3-[3-N-(4-bromobenzyl)benzamido]ethynyl-3-(3-cyclopentyloxy-4-methoxyphenyl)cyclohexan-1-one 21(a) methyl 3-iodobenzoate Methyl 3-iodobenzoate was prepared by standard chemistry well known to those versed in the art and is a white solid, m.p. 40–41° C. 21(0b) 3-(3-cyclopentyloxy-4-methoxyphenyl)-3-(3carbomethoxyphenyl)ethynyl-cyclohexan-1-one The title compound was prepared in a similar manner to the compound of Example 5b, starting from the compound of Example 3 (E1, 0.30 g, 0.96 mmol), as a clear yellow oil (0.43 g, 100%). $^1$H NMR(400 MHz, CDCl$_3$) δ8.07 (s, 1H), 7.96 (dd, J=7.8, 1.5Hz, 1H), 7.58 (dd, J=7.8, 1.5Hz, 1H), 7.38 (t, J=7.8Hz, 1H), 7.16 (d, J=2.2Hz, 1H), 7.06 (dd, J=8.43, 2.2Hz, 1H), 6.86 (d, J=8.43Hz, 1H), 4.80 (rn, 1H), 3.92 (s, 3H), 3.85 (s, 3H), 2.82 (dd, J=26, 13.6Hz, 2H), 2.50 (m, 1H), 2.42–2.15 (m, 4H), 2.05 (m, 1H), 1.90 (m, 6H), 1.62, (m, 3H).

20c) 3-(3-cyclopentyloxy-4-methoxyphenyl)-3-(3-carboxyphenyl)ethynyl-cyclohexan-1-one The title compound was prepared in a similar manner to the compound from Example 6, starting from the compound from Example 20c (0.43 g, 0.96 mmol), as a white solid (0.36 g, 87%), m.p. 82–84° C.

21(d) 3-[3-N-(4-bromobenzyl)benzamido]ethynyl-3-(3-cyclopentyloxy-4-methoxyphenyl)cyclohexan-1-one To a stirred mixture of the compound from Example 20c (0.36 g, 0.83 mmol), 1-hydroxybenzotriazole hydrate (Aldrich, 0.13 g, 0.91 mmol), 4-methylmorpholine (Aldrich, 0.19 mL, 1.7 mmol) and 4-bromobenzylamine hydrochloride (Aldrich, 0.20 g, 0.91 mmol) in dichloromethane (5 mL) under an argon atmosphere at 0° C. was added 1-(3 dimethylaminopropyl)-3-ethylcarbodiimide hydrochloride (Aldrich, 0.18 g, 0.91 mmol). After stiring 24 h at room temperature, water was added. The mixture was acidified with 3N hydrochloric acid, was extracted three times with dichloromethane, was washed once with water, was washed once with 10% aodium hydroxide, was dried (magnesium sulfate) and was evaporated. Purification by flash chromatography, eluting with 2:1 ethyl acetate/hexanes, followed by trituration from ether/hexanes provided the tide compound as a white solid (0.25 g, 50%), m.p. 98–100° C.

UTILITY EXAMPLES

EXAMPLE A

Inhibitory effect of compounds of Formula (I) and (II) on in vitro TNF production by human monocytes The inhibitory effect of compounds of Formula (I) and (II) on in vitro TNF production by human monocytes may be determined by the protocol as described in Badger et al., EPO published Application 0 411 754 A2, Feb. 6, 1991, and in Hanna, WO 90/15534, Dec. 27, 1990.

EXAMPLE B

Two models of endotoxic shock have been utilized to determine in vivo TNF activity for the compounds of Formula (l) and (II). The protocol used in these models is described in Badger et al., EPO published Application 0 411 754 A2, Feb. 6, 1991, and in Hanna, WO 90/15534, Dec. 27, 1990.

The compound of Example 1 herein demonstrated a positive in vivo response in reducing serum levels of TNF induced by the injection of endotoxin.

EXAMPLE C

Isolation of PDE Isozymes

The phosphodiesterase inhibitory activity and selectivity of the compounds of Formula (I) and (I) can be determined using a battery of five distinct PDE isozymes. The tissues used as sources of the different isozymes are as follows: 1) PDE Ib, porcine aorta; 2) PDE Ic, guinea-pig heart; 3) PDE m, guinea-pig heart; 4) PDE IV, human monocyte; and 5) PDE V (also called "Ia"), canine trachealis. PDEs Ia, Ib, Ic and m are partially purified using standard chromatographic techniques [Torphy and Cieslinski, Mol. Pharmacol., 37:206–214, 1990]. PDE IV is purified to kinetic homogeneity by the sequential use of anion-exchange followed by heparin-Sepharose chromatography [Torphy et al., J. Biol. Chem., 267:1798–1804, 1992].

Phosphodiesterase activity is assayed as described in the protocol of Torphy and Cieslinski, Mol. Pharmacol., 37:206–214, 1990. Positive IC$_{50}$'s in the nanomolar to μM range for compounds of the workings examples described herein for Formula (I) and (II) have been demonstrated.

What is claimed is:

1. A compound of Formula (I)

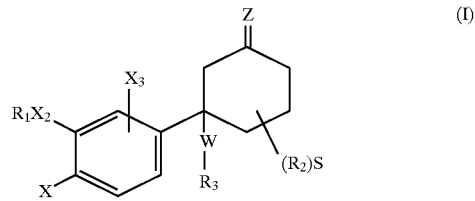

(I)

wherein:

R$_1$ is —(CR$_4$R$_5$)$_n$C(O)O(CR$_4$R$_5$)$_m$R$_6$, —(CR$_4$R$_5$)$_n$C(O)NR$_4$(CR$_4$R$_5$)$_m$R$_6$, —(CR$_4$R$_5$)$_n$O(CR$_4$R$_5$)$_m$R$_6$, or —(CR$_4$R$_5$)$_r$R$_6$ wherein the alkyl moieties may be unsubstituted or substituted with one or more fluorines;

m is 0 to 2;

n is 0 to 4;

r is 0 to 6;

R$_4$ and R$_5$ are independently hydrogen or C$_{1-2}$ alkyl;

R$_6$ is hydrogen, methyl, hydroxyl, aryl, halo substituted aryl, aryloxyC$_{1-3}$ alkyl, halo substituted aryloxyC$_{1-3}$ alkyl, indanyl, indenyl C$_{7-11}$ polycycloalkyl, tetrahydrofuranyl, furanyl, tetrahydropyranyl, pyranyl, tetrahydrothienyl, thienyl, tetrahydrothiopyranyl, thiopyranyl, C$_{3-6}$ cycloalkyl, or a C$_{4-6}$ cycloalkyl containing one or two unsaturated bonds, wherein the cycloalkyl or heterocyclic moiety may be unsubstituted or substituted by 1 to 3 methyl groups, one ethyl group, or an hydroxyl group;

provided that:
a) when $R_6$ is hydroxyl, then m is 2; or
b) when $R_6$ is hydroxyl, then r is 2 to 6; or
c) when $R_6$ is 2-tetrahydropyranyl, 2-tetrahydrothiopyranyl, 2-tetrahydrofuranyl, or 2-tetrahydrothienyl, then m is 1 or 2; or
d) when $R_6$ is 2-tetrahydropyranyl, 2-tetrahydrothiopyranyl, 2-tetrahydrofuranyl, or 2-tetrahydrothienyl, then r is 1 to 6;
e) when n is 1 and m is 0, then $R_6$ is other than H in —$(CR_4R_5)_nO(CR_4R_5)_mR_6$;

X is $YR_2$, fluorine, $NR_4R_5$, or formyl amine;
Y is O or $S(O)_{m'}$;
m' is 0, 1, or 2;
$X_2$ is O or $NR_8$;
$X_3$ is hydrogen or X;
$R_2$ is independently selected from —$CH_3$ or —$CH_2CH_3$ unsubstituted or substituted by 1 or more fluorines;
s is 0 to 4;
$R_3$ is $COOR_{14}$, $C(O)NR_4R_{14}$ or $R_7$;
W is alkyl of 2 to 6 carbons, alkenyl of 2 to 6 carbon atoms or alkynyl of 2 to 6 carbon atoms;
Z is O, $NR_7$, $NCR_4R_5C_{2-6}$ alkenyl $NOR_{14}$, $NOR_{15}$, $NOCR_4R_5C_{2-6}$ alkenyl, $NNR_4R_{14}$, $NNR_4R_{15}$, NCN, $NNR_8C(O)NR_8R_{14}$, $NNR_8C(S)NR_8R_{14}$, or =Z is 2-(1,3-dithiane), 2-(1,3-dithiolane), dimethylthio ketal, diethylthio ketal, 2-(1,3-dioxolane), 2(1,3dioxolane), 2-(1,3-oxathiolane), dimethyl ketal or diethyl ketal;
$R_7$ is —$(CR_4R_5)_qR_{12}$ or $C_{1-6}$ alkyl wherein the $R_{12}$ or $C_{1-6}$ alkyl group is unsubstituted or substituted one or more times by methyl or ethyl unsubstituted or substituted by 1–3 fluorines, —F, —Br, —Cl, —$NO_2$, —$NR_{10}R_{11}$, —$C(O)R_8$, —$CO_2R_8$, —$O(CH_2)_{2-4}OR_8$, —$O(CH_2)_qR_8$, —CN, —$C(O)NR_{10}R_{11}$, —$O(CH_2)_qC(O)NR_{10}R_{11}$, —$O(CH_2)_qC(O)R_9$, —$NR_{10}C(O)NR_{10}R_{11}$, —$NR_{10}C(O)R_{11}$, —$NR_{10}OC(O)OR_9$, —$NR_{10}C(O)R_{13}$, —$C(NRO)NR_{10}R_{11}$, —$C(NCN)NR_{10}R_{11}$, —$C(NCN)SR_9$, —$NR_{10}C(NCN)SR_9$, —$NR_{10}C(NCN)NR_{10}R_{11}$, —$NR_{10}S(O)_2R_9$, —$S(O)_{m'}R_9g$, —$NR_{10}C(O)C(O)NR_{10}R_{11}$, —$NR_{10}C(O)C(O)R_{10}$, or $R_{13}$;
q is 0, 1, or 2;
$R_{12}$ is $R_{13}$, $C_3$–$C_7$ cycloalkyl, (2-, 3- or 4pyridyl), pyrimidyl, pyrazolyl, (1- or 2-imidazolyl), pyrrolyl, piperazinyl, piperidinyl, morpholinyl, furanyl, (2- or 3-thienyl), quinolinyl, naphthyl, or phenyl;
$R_8$ is hydrogen or $R_9$;
$R_9$ is $C_{1-4}$ alkyl unsubstituted or substituted by one to three fluorines;
$R_{10}$ is $OR_8$ or $R_{11}$;
$R_{11}$ is hydrogen, or $C_{1-4}$ alkyl unsubstituted or substituted by one to three fluorines; or when $R_{10}$ and $R_{11}$ are as $NR_{10}R_{11}$ they may together with the nitrogen form a 5 to 7 membered ring optionally containing at least one additional heteroatom selected from O, N, or S;
$R_{13}$ is a substituted or unsubstituted heteroaryl group selected from the group consisting of oxazolidinyl, oxazolyl, thiazolyl, pyrazolyl, triazolyl, tetrazolyl, imidazolyl, imidazolidinyl, thiazolidinyl, isoxazolyl, oxadiazolyl, and thiadiazolyl, and where $R_{13}$ is substituted on $R_{12}$ or $R_{13}$ the rings are connected through a carbon atom and each second $R_{13}$ ring may be unsubstituted or substituted by one or two $C_{1-2}$ alkyl groups unsubstituted or substituted on the methyl with 1 to 3 fluoro atoms;

$R_{14}$ is hydrogen or $R_7$; or when $R_8$ and $R_{14}$ are as $NR_8R_{14}$ they may together with the nitrogen form a 5 to 7 membered ring optionally containing one or more additional heteroatoms selected from O, N, or S;
$R_{15}$ is $C(O)R_{14}$, $C(O)NR_4R_{14}$, $S(O)_2R_7$, or $S(O)_2NR_4R_{14}$;
provided that:
(f) $R_7$ is not $C_{1-4}$ alkyl unsubstituted or substituted by one to three fluorines; or the pharmaceutically acceptable salts thereof.

2. A compound according to claim 1 wherein $R_1$ is —$CH_2$-cyclopropyl, -cyclopentyl, -3-hydroxycyclopentyl, methyl or $CF_2H$; X is $YR_2$; Y is oxygen; $X_2$ is oxygen; $X_3$ is hydrogen; $R_2$ is $CF_2H$ or methyl, W is ethynyl or 1,3-butadiynyl, $R_3$ is a substituted or unsubstituted pyrimidinyl ring, X is $YR_2$, and Z is O, $NR_7$.

3. A compound according to claim 1 wherein $R_1$ is —$CH_2$-cyclopropyl, -cyclopentyl, -3-hydroxycyclopentyl, methyl or $CF_2H$; X is $YR_2$; Y is oxygen; X2 is oxygen; $X_3$ is hydrogen; $R_2$ is $CF_2H$ or methyl, W is ethynyl or 1,3-butadiynyl, $R_3$ $R_3$ is $R_7$ where $R_7$ is an unsubstituted or substituted aryl or heteroaryl ring, excluding pyridiminyl, X is $YR_2$, and Z is O.

4. A compound according to claim 1 which is
(+/−) 3-(3-cyclopentyloxy-4-methoxyphenyl)-3-phenylethynylcyclohexan-1-one,
(+/−) 3-(3-cyclopentyloxy-4-methoxyphenyl)-3-(3-carbomethoxyphenyl)ethynylcyclohexan-1-one,
(+/−) 3-(3-carboxyphenylethynyl)-3-(3-cyclopentyloxy-4-methoxyphenyl)cyclohexan-1-one,
3-(3-cyclopentyloxy-4-methoxyphenyl)-3[3-(5-methyl-[1,3,4]thiadiazol-2-yl)phenylethynyl]cyclohexan-1-one, 3-(3-cyclopentyloxy-4-methoxyphenyl)-3-[3-(5-methyl-[1,3,4]oxadiazol-2-yl)phenylethynyl]cyclohexan-1-one, 3-(3-cyclopentyloxy-4-methoxyphenyl)-3-[3-(3-methyl-[1,2,4]oxadiazol-5-yl)phenylethynyl]cyclohexan-1-one, 3-(3-cyclopentyloxy-4-methoxyphenyl)-3-[3-(5-methyl-[1,2,4]oxadiazol-3-yl)phenylethynyl]cyclohexan-1-one,
3-(3-cyclopentyloxy-4-methoxyphenyl)-3-(3-cyanophenylethynyl)cyclohexan-1 -one,
3-(3-cyclopentyloxy-4-methoxyphenyl)-3-(3-nitrophenylethynyl)cyclohexan-1-one,
3-(3-cyclopentyloxy-4-methoxyphenyl)-3-(2-hydroxyethoxyphenylethynyl)cyclohexan-1-one,
3-(3-acetamidophenylethynyl)-3-(3-cyclopentyloxy-4-methoxyphenyl)cyclohexan-1-one,
3-(3-cyclopentyloxy-4-methoxyphenyl)-3-(3-methanesulfonamidophenylethynyl)cyclohexan-1-one,
3-(3-aminophenylethynyl)-3-(3-cyclopentyloxy-4-methoxyphenyl)cyclohexan-1-one,
(+/−)-3-(4-carboxyphenylethynyl)-3-(3-cyclopentyloxy-4-methoxyphenyl)cyclohexan-1-one,
3-(3-cyclopentyloxy-4-methoxyphenyl)-3-[3-(5-trifluoromethyl-1,2,4]oxadiazol-3-yl)phenylethynyl)cyclohexan-1 -one,
(+) and (−) 3-(3-cyclopentyloxy-4-methoxyphenyl)-3-phenylethynylcyclohexan-1-one, or
3-[3-N-(4-bromobenzyl)benzamido]ethynyl-3-(3-cyclopentyloxy-4-methoxyphenyl)cyclohexan-1-one.

5. A pharmaceutically acceptable composition comprising a compound according to either of Formula I according to claims 1 and a pharmaceutically acceptable excipient.

6. A method for treating asthma which comprises administering to a mammal in need thereof an effective amount of a compound of Formula (I) according to claim 1 alone or admixed with a pharmaceutical excipient.

7. A compound of Formula II

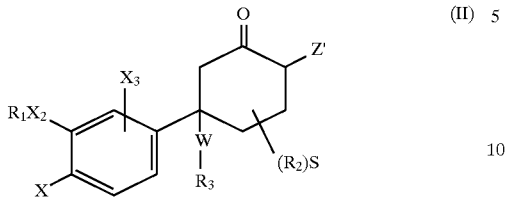

wherein:

$R_1$ is $-(CR_4R_5)_nC(O)O(CR_4R_5)_mR_6$, $-(CR_4R_5)_nC(O)NR_4(CR_4R_5)_mR_6$, $-(CR_4R_5)_nO(CR_4R_5)_mR_6$, or $-(CR_4R_5)_rR_6$ wherein the alkyl moieties may be unsubstituted or substituted with one or more fluorines;

m is 0 to 2;

n is 0 to 4;

r is 0 to 6;

$R_4$ and $R_5$ are independently hydrogen or $C_{1-2}$ alkyl;

$R_6$ is hydrogen, methyl, hydroxyl, aryl, halo substituted aryl, aryloxy $C_{1-3}$ alkyl, halo substituted aryloxy $C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl or heterocyclic moiety is unsubstituted or substituted by 1 to 3 methyl groups, an ethyl group, or an hydroxyl group;

provided that:
 a) when $R_6$ is hydroxyl, then m is 2; or
 b) when $R_6$ is hydroxyl, then r is 2 to 6; or
 c) when $R_6$ is 2-tetrahydropyranyl, 2-tetrahydrothiopyranyl, 2-tetrahydrofuranyl, or 2-tetrahydrothienyl, then m is 1 or 2; or
 d) when $R_6$ is 2-tetrahydropyranyl, 2-tetrahydrothiopyranyl, 2-tetrahydrofuranyl, or 2-tetrahydrothienyl, then r is 1 to 6;
 e) when n is 1 and m is 0, then $R_6$ is other than H in $-(CR_4R_5)_nO(CR_4R_5)_mR_6$;

X is $YR_2$, fluorine, $NR_4R_5$, or formyl amine;

Y is O or $S(O)_{m'}$;

m' is 0, 1, or 2;

$X_2$ is O or $NR_8$;

$X_3$ is hydrogen or X;

$R_2$ is independently selected from $-CH_3$ or $-CH_2CH_3$ unsubstituted or substituted by 1 or more fluorines;

s is 0 to 4;

$R_3$ is $COOR_{14}$, $C(O)NR_4R_{14}$ or $R_7$;

W is alkyl of 2 to 6 carbons, alkenyl of 2 to 6 carbon atoms or alkynyl of 2 to 6 carbon atoms;

Z' is $C(Y')R_{14}$, $C(O)OR_{14}$, $C(Y')NR_{10\ R14}$, $C(NR_{10})NR_{10}R_{14}$, CN, $C(NOR_8)R_{14}$, $C(O)NR_8NR_8C(O)R_8$, $C(O)NR_8NR_{10}R_{14}$, $C(NOR_{14})R_8$, $C(NR_8)NR_{10}R_{14}$, $C(NR_{14})NR_8R_8$ $C(NCN)NR_{10}R_{14}$, $C(NCN)SR_9$, (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, or 5-oxazolidinyl), (2-, 4-, or 5-thiazolidinyl), or (2-, 4-, or 5-imidazolidinyl); wherein all of the heterocylic ring systems may be optionally substituted one or more times by $R_{14}$;

Y' is O or S;

$R_7$ is $-(CR_4R_5)_qR_{12}$ or $C_{1-6}$ alkyl wherein the $R_{12}$ is phenyl or $C_{1-6}$ alkyl group is unsubstituted or substituted one or more times by $C_{1-2}$ alkyl unsubstituted or substituted by one to three fluorines, $-F$, $-Br$, $-Cl$, $-NO_2$, $-Si(R_4)_3$, $-NR_{10}R_{11}$, $-C(O)R_8$, $-O(CH_2)_{2-4}OR_8$, $-CO_2R_8$, $-OR_8$, $-CN$, $-C(O)NR_{10}R_{11}$, $-OC(O)NR_{10}R_{11}$, $-OC(O)R_8$, $-NR_{10}C(O)NR_{11}$, $-NR_{10}C(O)R_{11}$, $-NR_{10}C(O)OR_9$, $-NR_{10}C(O)R_{13}$, $-C(NR_{10})NR_{10}R_{11}$, $-C(NCN)NR_{10}R_{11}$, $-C(NCN)SR_9$, $-NR_{10}C(NCN)SR_9$, $-NR_{10}C(NCN)NR_{10}R_{11}$, $-NR_{10}S(O)_2R_9$, $-S(O)_{m'}R_9$, $-NR_{10}C(O)C(O)NR_{10}R_{11}$, $-NR_{10}C(O)C(O)R_{10}$, thiazolyl, imidazolyl, oxazolyl, pyrazolyl, triazolyl, or tetrazolyl;

q is 0, 1, or 2;

$R_{12}$ is $R_{13}$, $C_{3-7}$ cycloalkyl, (2-, 3- or 4pyridyl), pyrimidyl, pyrazolyl, (1- or 2-imidazolyl), thiazolyl, triazolyl, pyrrolyl, piperazinyl, piperidinyl, morpholinyl, furanyl, (2- or 3-thienyl), (4- or 5-thiazolyl), quinolinyl, naphthyl, or phenyl;

$R_8$ is independently selected from hydrogen or $R_9$;

$R_9$ is $C_{1-4}$ alkyl unsubstituted or substituted by one to three fluorines;

$R_{10}$ is $OR_9$ or $R_{11}$;

$R_{11}$ is hydrogen, or $C_{1-4}$ alkyl unsubstituted or substituted by one to three fluorines; or when $R_{10}$ and $R_{11}$ are as $NR_{10}R_{11}$ they may together with the nitrogen form a 5 to 7 membered ring optionally containing at least one additional heteroatom selected from O, N, or S;

$R_{13}$ is a substituted or unsubstituted heteroaryl group selected from the group consisting of oxazolidinyl, oxazolyl, thiazolyl, pyrazolyl, triazolyl, tetralyl, imidazolyl, imidazolidinyl, thiazolidinyl, isoxazolyl, oxadiazolyl, and thiadiazolyl, and where $R_{13}$ is substituted on $R_{12}$ or $R_{13}$ the rings are connected through a carbon atom and each second $R_{13}$ ring may be unsubstituted or substituted by one or two $C_{1-2}$ alkyl groups unsubstituted or substituted on the methyl with 1 to 3 fluoro atoms;

$R_{14}$ is hydrogen or $R_7$; or when $R_8$ and $R_{14}$ are as $NR_8R_{14}$ they may together with the nitrogen form a 5 to 7 membered ring optionally containing one or more additional heteroatoms selected from O, N, or S;

provided that:
 (f) $R_7$ is not $C_{1-4}$ alkyl unsubstituted or substituted by one to three fluorines; or the pharmaceutically acceptable salts thereof.

8. A compound according to claim 7 wherein $R_1$ is $-CH_2$-cyclopropyl, -cyclopentyl, -3-hydroxycyclopentyl, methyl or $CF_2H$; X is $YR_2$; Y is oxygen; $X_2$ is oxygen; $X_3$ is hydrogen; $R_2$ is $CF_2H$ or methyl, W is ethynyl or 1,3-butadiynyl, $R_3$ is a substituted or unsubstituted pyrimidinyl ring, X is $YR_2$, and Z is O, $NR_7$.

9. A pharmaceutically acceptable composition comprising a compound according to either of Formula II according to claims 8 and a pharmaceutically acceptable excipient.

* * * * *